(12) United States Patent
Ratner et al.

(10) Patent No.: US 11,071,897 B2
(45) Date of Patent: Jul. 27, 2021

(54) SPORTS REACTION TIME SIMULATOR

(71) Applicants: Harvey Ratner, Silver Spring, MD (US); Wade Freeman, Bristow, VA (US)

(72) Inventors: Harvey Ratner, Silver Spring, MD (US); Wade Freeman, Bristow, VA (US)

( * ) Notice: Subject to any disclaimer, the term of this patent is extended or adjusted under 35 U.S.C. 154(b) by 471 days.

(21) Appl. No.: 15/935,300

(22) Filed: Mar. 26, 2018

(65) Prior Publication Data

US 2018/0272214 A1 Sep. 27, 2018

Related U.S. Application Data

(60) Provisional application No. 62/477,078, filed on Mar. 27, 2017.

(51) Int. Cl.
| | |
|---|---|
| *A63B 69/00* | (2006.01) |
| *A63B 71/06* | (2006.01) |
| *A61B 5/16* | (2006.01) |
| *A63B 24/00* | (2006.01) |

(52) U.S. Cl.
CPC .......... *A63B 69/0002* (2013.01); *A61B 5/162* (2013.01); *A63B 69/0053* (2013.01); *A63B 71/06* (2013.01); *A63B 71/0622* (2013.01); *A61B 5/163* (2017.08); *A61B 2503/10* (2013.01); *A63B 24/0062* (2013.01); *A63B 24/0075* (2013.01); *A63B 2069/0008* (2013.01); *A63B 2071/0694* (2013.01); *A63B 2210/50* (2013.01); *A63B 2220/62* (2013.01); *A63B 2220/805* (2013.01); *A63B 2225/50* (2013.01); *A63B 2225/74* (2020.08)

(58) Field of Classification Search
CPC .................................................. A63B 69/0002
USPC ......................................................... 434/247
See application file for complete search history.

(56) References Cited

U.S. PATENT DOCUMENTS

| | | |
|---|---|---|
| 4,461,477 A | 7/1984 | Stewart |
| 4,824,237 A | 4/1989 | Ratner et al. |
| 4,913,432 A | 4/1990 | Barra |
| 5,060,941 A | 10/1991 | Barra |
| 5,261,659 A | 11/1993 | Tierney |
| 5,812,239 A | 9/1998 | Eger |
| 6,016,038 A * | 1/2000 | Mueller ................ H05B 45/46 315/291 |
| 7,300,388 B2 | 11/2007 | Sams, III |
| 7,353,071 B2 | 4/2008 | Blackwell et al. |

(Continued)

*Primary Examiner* — Kesha Frisby
(74) *Attorney, Agent, or Firm* — Edell, Shapiro & Finnan, LLC

(57) ABSTRACT

A method and system for testing and improving a user's visual tracking skills and reaction time to a moving object includes simulating motion of an object by individually illuminating LEDs in longitudinal sequence along individually selectable paths having different positional approaches toward a target. A user activates a switch or interrupts a beam with the intent of terminating the sequence in time coincidence with illumination of a designated LED proximate the target. A microprocessor detects the time difference between illumination of the designated LED and termination of the sequence by the user as measure of the user's visual tracking and reaction time. In one embodiment the user is a baseball batter, the target is a home plate and the selectable paths are simulations of straight and breaking pitches.

14 Claims, 13 Drawing Sheets

(56) References Cited

U.S. PATENT DOCUMENTS

| | | |
|---|---|---|
| 7,380,791 B2 | 6/2008 | Gauselmann et al. |
| 7,547,214 B2 | 6/2009 | Duesterhoeft et al. |
| 7,575,526 B2 | 8/2009 | Husband |
| 8,430,547 B2 | 4/2013 | Reichow et al. |
| 8,702,265 B2 | 4/2014 | May |
| 9,039,548 B2 | 5/2015 | Sams, III |
| 2011/0241559 A1 | 10/2011 | Grajcar |
| 2013/0172129 A1 | 7/2013 | Sams, III |
| 2014/0290824 A1* | 10/2014 | Goldwater ................ F21S 4/22 156/60 |
| 2014/0307438 A1 | 10/2014 | Pearson et al. |
| 2014/0362574 A1 | 12/2014 | Barrett |
| 2015/0301781 A1 | 10/2015 | Ekkaia et al. |

* cited by examiner

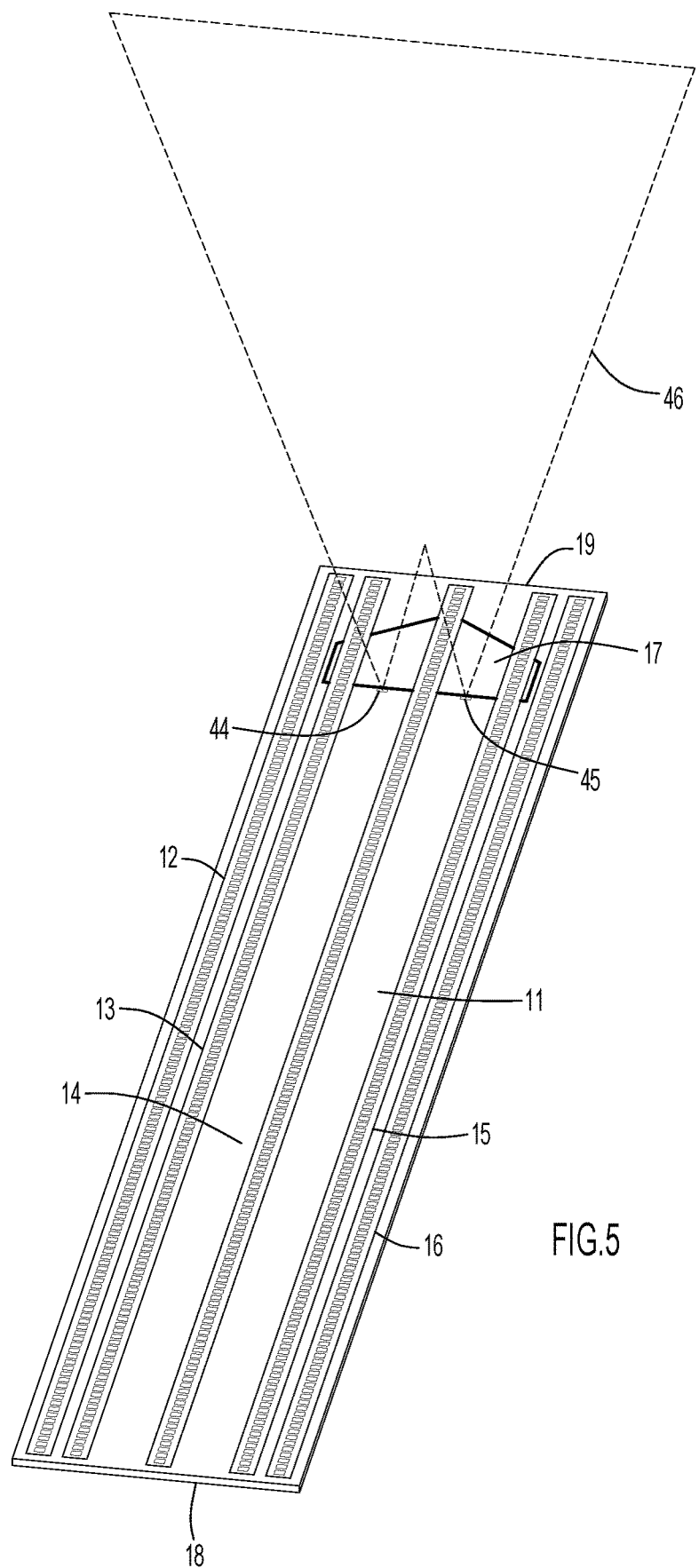

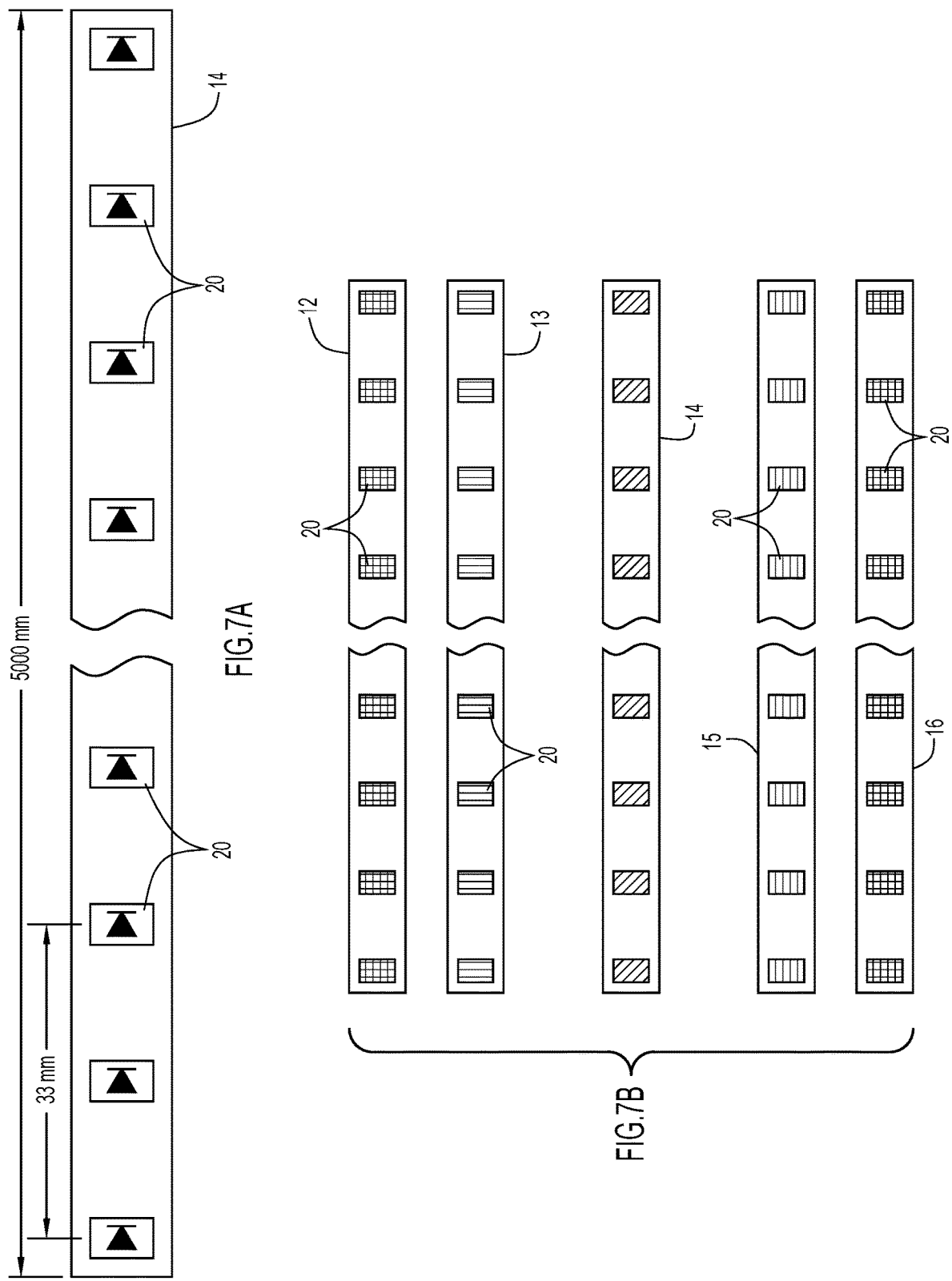

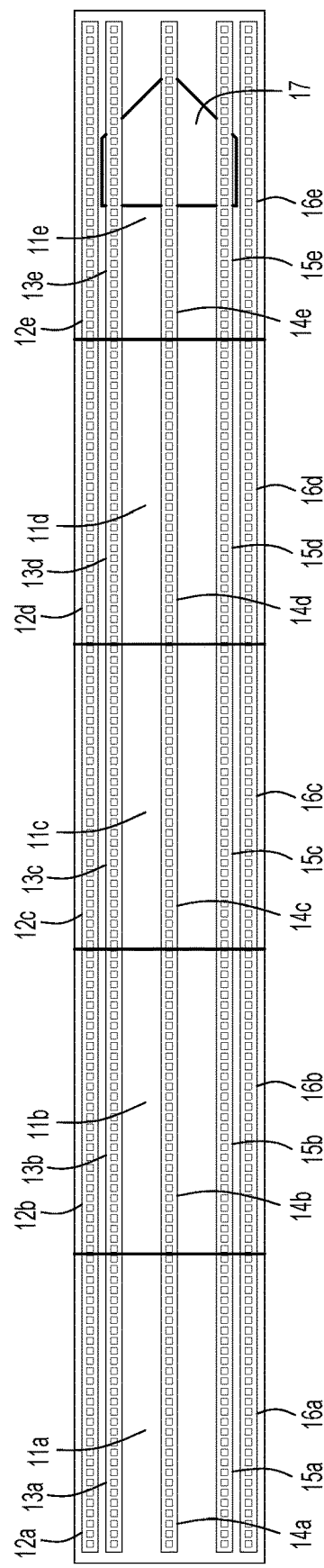
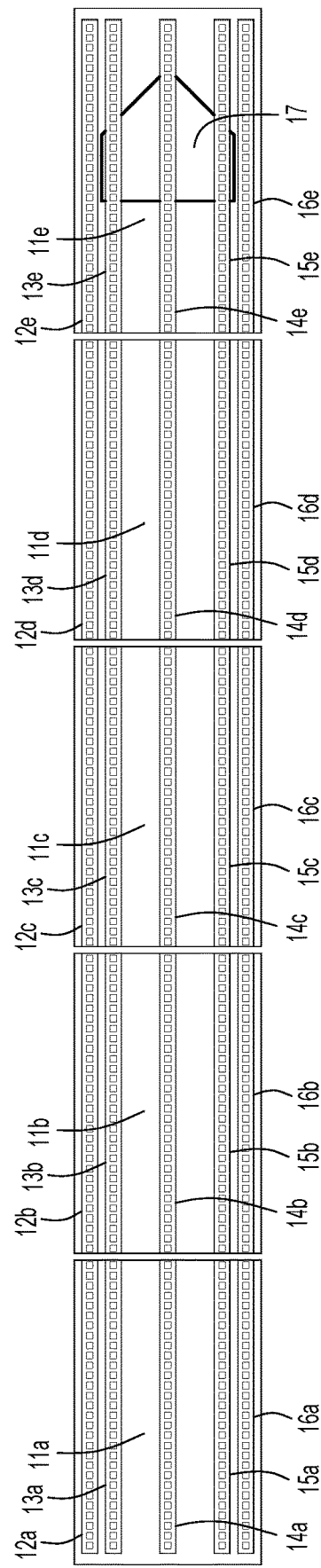
FIG.10A
FIG.10B

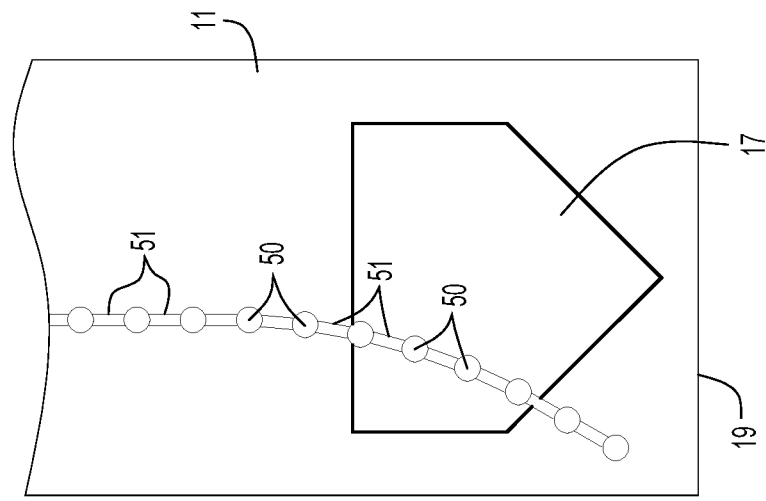
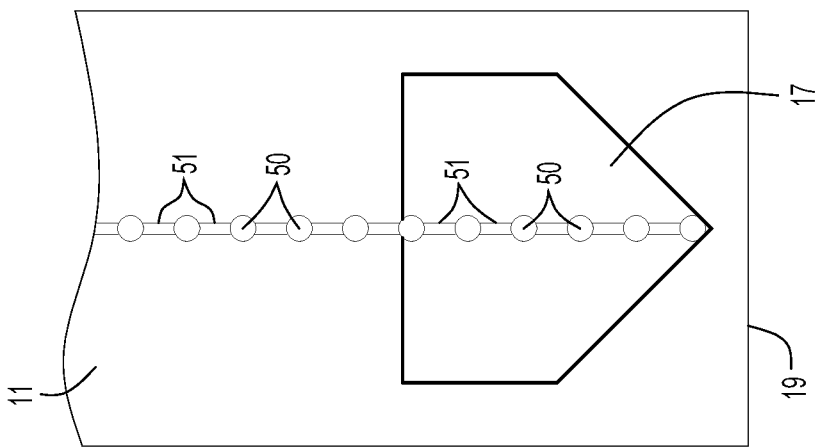
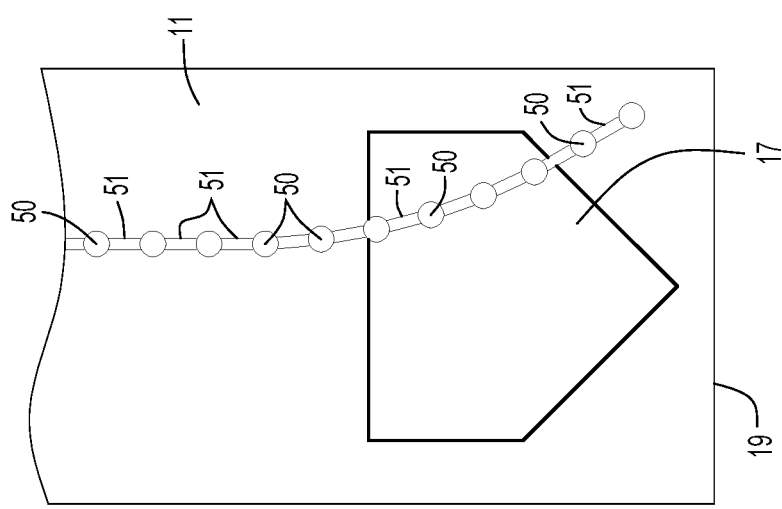

SPORTS REACTION TIME SIMULATOR

CROSS REFERENCE TO RELATED APPLICATIONS

The present application is a non-provisional application based on and claiming priority from U.S. Provisional Application No. 62/477,078, entitled "Sports Reaction Time Simulator" and filed Mar. 27, 2017, the disclosure in which is hereby incorporated herein by reference in its entirety.

FIELD OF THE INVENTION

The present invention relates generally to a training devices and systems for enhancing eye movement, hand-eye coordination and eye tracking skills and, in exemplary embodiments, to a training device and system and a method for simulating different speeds and movements of various types of pitches to enhance ocular conditioning and the timing of pitch striking skills of a baseball or softball player. Although exemplary embodiments of the present invention are described herein primarily in connection with a batter's reaction to a pitched baseball or softball, it is to be understood that the principles of the present invention apply to any activity requiring an ability to visually track and quickly react a moving object.

BACKGROUND OF THE INVENTION

It is a widely held belief that the skill of hitting a baseball or softball (particularly a fast pitch softball) is not only one of the most difficult skills in sports to master, but is one of the most difficult to practice. Moreover, it is well known to those involved in the sports of baseball and fast pitch softball that the skill of a batter is determined by several factors, including the batter's ability to track a pitched ball from a pitcher's release point to the ideal bat-ball contact point at home plate, and the batter's ability to react quickly (reaction time) once a decision is made to swing at a pitched ball such that contact of the bat and ball takes place as the ball moves into a prescribed "impact or strike zone" proximate home plate.

Improving visual tracking skills and reaction time of a batter can provide a competitive advantage and/or enhance a batter's ability to properly hit a pitched ball. Specifically, a batter that is able to visually pick up a pitched ball more quickly after it is released by the pitcher, track the ball's speed and direction, maintain focus until the ball reaches home plate, will have more time to react to and make optimum contact with the ball and determine whether it is in the strike zone than another batter having the same physical attributes but poorer visual pick up and tracking skills.

A variety of different types of visual training devices/systems has been developed for different types of sports to enhance eye-hand coordination, dynamic visual acuity, visual recognition skills, depth perception, focusing and reaction time of an athlete. Many of these training devices/systems can be employed by athletes to develop eye movement and tracking skills used to strike a moving object, such as, for example, a baseball or softball with a bat, a hockey puck with a stick, a tennis ball with a racket, etc. See, for example, U.S. Pat. No. 9,039,548 (Sams, III), U.S. Pat. No. 8,430,547 (Reichow et al.), U.S. Pat. No. 7,841,950 (Davidson et al.), U.S. Pat. No. 7,326,060 (Seller et al.), U.S. Pat. No. 5,261,659 (Tierney), U.S. Pat. No. 4,824,237 (Ratner et al.), and U.S. Pat. No. 4,461,477 (Stewart), as well as U.S. Patent Publication Nos. 2013/0172129 (Sams, III) and 2011/0224027 (Edmondson); the entire contents of those patents and published applications are incorporated herein by reference.

In the patent to Sams, III, a swing training device includes a cable with series of sequentially timed light emitting diodes (LED's) defining a track that simulates the movement of a pitched ball along a horizontal path and serving as a cue to initiate a swing. The device helps develop visual skills by conditioning the eyes to track the lights as they are sequentially illuminated along the path to a stationary ball such that a batter can train to strike the stationary ball when the light sequence reaches the stationary ball. A computer device with a microprocessor is used to control the timing of the LED lights.

In the patent to Reichow, a device for training an individual's visual abilities includes a raised rigid support or table on which a plurality of light sources are mounted and individually actuated under the control of a control unit. The control unit may be configured to activate the light sources in a sequential manner to simulate a variety of environments, such as a baseball game. For example, the light actuation sequence may mimic a ball thrown between a simulated pitcher's mound and a batter/trainee at a simulated home plate. Once the pitched ball, simulated by a sequence of individually actuated lights, arrives at home plate, a trainee attempts to concurrently actuate an input device (e.g., swing a bat or generate a movement) to create an input signal at the time appropriate time to simulate bat contact.

Similarly, the patent to Tierney discloses a batter training device capable of simulating the path, speed, movement, location and visual perception of a ball on its path to home plate by means of a plurality of individually placed and sequentially timed light sources of approximate baseball size. The light sources are supported on individually movable and height adjustable supports that can be positioned by a user to simulate the trajectory of a pitched ball of any type, e.g., a fastball, a curve ball, a sinker ball, etc., starting at the release point of the pitcher and culminating at the ideal bat-ball contact point at home plate. A timer controls individual activation of the plurality of lights sources.

The Ratner patent discloses another device for testing vision and eye-hand coordination of a human subject. In that device, a multiplicity of lamps extend in a linear array along a pole which is securable at a proximal end to a support so as to extend horizontally at an adjustable height. Timing pulses from a control unit momentarily and sequentially illuminate the lamps in the linear array. The lamps are spaced and illuminated in a sequence to simulate a sports activity, such as a thrown baseball, a stroked tennis ball, a moving hockey puck, etc. A lamp at a distal end of the pole is associated with an impact switch that is housed in a bumper and that is momentarily actuated when it is impacted such as by a bat, stick, racquet, etc. The human subject strikes the bumper when the last lamp is directly illuminated to effect a switch closure that is monitored relative to the time of illumination of the last lamp to determine whether the impact was early, late or at the proper time.

The Stewart patent discloses apparatus for monitoring the response time and improving the performance of a baseball or softball batter. The apparatus can comprise a sequence of lights which may be mounted on a horizontal table or suspended from above such that the sequence of illuminating lights appears to approach the batter as though it was a ball traveling from a pitcher's mound. The lights are sequentially actuated by a controller. After the last light of the sequence is illuminated, either a "strike" light or a "ball" light is illuminated to instruct the batter whether to swing or not. When the strike light is illuminated and the batter swings the bat, the response time between the instant the last light of the sequence is illuminated and the batter's swing is determined and provided to a display panel.

While the devices described in the aforementioned prior art patents and publications may fulfill their stated objectives to some extent, they are limited in that they cannot simulate different types of pitches (e.g., fast balls, sliders, curve balls, etc.) without rearranging or repositioning the actuable light sources for each such pitch. Even simulated straight fast balls cannot be directed to different width locations at home plate without light source rearrangement. This is highly disadvantageous for training since the batter-trainee always knows in advance the type and location of the simulated pitch. In addition, the prior devices lack portability and are therefore not readily set up and useable in different locations. Thus, there exists a need for an improved training device with all the benefits described above.

Although embodiments of the present invention described herein are focused on training for baseball and softball, it is to be understood that embodiments of the present invention can be used, with only minor modifications, if any, for training tennis players and players, hockey, lacrosse, soccer and water polo goalies, and other sports in which a fast moving object must be visually tracked and reacted to either by striking or catching that object.

SUMMARY OF THE INVENTION

Accordingly, it is an object of the present invention to provide an improved to provide a method and system for testing and improving a user's visual tracking skills and reaction time to an approaching moving object intended to be caught or struck.

In accordance with one aspect of the invention, a system for testing and improving a user's visual tracking skills and reaction time to a moving object includes an elongated structure having a top surface, an origin location and a target longitudinally spaced from the origin location. A plurality of longitudinally extending tracks are secured to the structure and extend longitudinally between the origin location and target, each track comprising a series of longitudinally spaced individually actuable light sources, e.g., LEDs. The tracks are transversely spaced at the target by less than the target width such that at least a first of the tracks intersects the target and at least a second track passes the target without intersecting it. A controller includes a microprocessor or other CPU connected to control sequential momentary actuation of the light sources in accordance with multiple individually selectable paths, each path comprising a respective longitudinal actuation sequence of light sources along one or more of the tracks to simulate longitudinal motion of the moving object. At least some of the selectable paths include light sources in only one track, and others of the selectable paths include light sources in at least two tracks. A user actuator is in electrical communication with the controller to enable termination by the user at any time of a then active light actuation sequence. One of the light sources may be selected as a designated object light source based on its location relative to the target, and the user may be tasked with actuating the user actuator in time coincidence with actuation of the object light source during a light actuation sequence. In such an arrangement the processor is configured to determine the user's reaction time by measuring the time between actuation of the object light source and actuation of the user actuator. The light sources are preferably individually addressable LEDs of the RGB type, capable of selectively emitting light in any of a variety of colors, and the tracks are preferably commonly available LED strips. In one preferred embodiment, all of the LEDs in any given track emit light of the same color, although that color may be selectively changed.

In one embodiment, configured for testing and visually tracking the moving object as a simulated baseball pitch, the target is a standard home plate and at least some of the selectable paths simulate a straight pitch and others simulate a curved (i.e., breaking) pitch. The plurality of tracks may comprise five parallel tracks including a first center track longitudinally bisecting the home plate target, second and third inboard tracks disposed transversely equally spaced from and on opposite sides of the first track and intersecting the home plate target, and fourth and fifth outboard tracks disposed transversely equally spaced from and on opposite sides of the center track and transversely spaced from the home plate target. The system may be portable by providing the tracks on a surface of a roll up mat or on connectable rigid sections containing respective length sections of the tracks.

In accordance with another aspect of the invention a method for testing and improving a user's visual tracking skills and reaction time to a moving object comprises simulating motion of an object between an origin location and a spaced target by individually illuminating light sources in longitudinal sequence, the light sources being disposed in a coplanar array of multiple light sources along a selected one of several possible individually selectable paths between the origin location and the target. Only some of the light sources in the array are illuminated in each selected path, and some of the paths intersect the target at different transverse locations. A user actuator may be actuated by a user when the longitudinal sequence illuminates a selectively designated object light source located proximate the target, and the time of user actuation is detected so that the time difference between that actuation and the illumination of the designated object light source can be determined. The array may be arranged as a plurality of parallel tracks of light sources (e.g., LEDs) extending between the origin location and target such that at least one track intersects the target. At least some of the paths include light sources in only one track and others include light sources in at least two tracks. The moving object may be a simulated baseball pitch, the target may be a standard home plate, and least some paths simulate a straight pitch while others simulate a breaking pitch. The light sources in may be programmed so that all of the light sources in any given track emit a specified color for that track that can change from pitch to pitch or from user to user.

Terminology

It is to be understood that, unless otherwise stated or contextually evident, as used herein:

The term "longitudinal" refers to the direction along the length of the light source tracks described herein.

The terms "transverse" and "lateral" refer to the horizontal direction perpendicular to the longitudinal direction.

The terms "top", "bottom", "vertical", "horizontal", etc., are used for convenience to refer to the orientation of the tracks and their support in use and are not intended to otherwise limit the structures described and claimed.

The phrase "individually illuminating", and the like, as used herein means illuminating light sources one at a time.

The phrase "electrical communication" refers to the ability to transmit signals between components, whether by wire connection, wireless transmission, or other means.

BRIEF DESCRIPTION OF THE DRAWINGS

FIG. 5 is a perspective view from above showing the mat and target of FIG. 1 employed with plural energy beam transceivers.

FIG. 7A is an exploded view in plan from above showing one of the LED tracks on the mat of FIG. 1.

FIG. 7B is an exploded view in plan of a portion of the mat of FIG. 1 showing the LEDs in some tracks having different colors from the LEDs in other tracks.

FIG. 10A is a plan view from above of another embodiment of the invention in which the tracks of LEDs are formed on a plurality (e.g., five) substantially rigid panels that are separable for portability.

FIG. 10B is a plan view from above of the embodiment of FIG. 10A showing the boards separated from one another prior to assembly.

FIGS. 12A, 12B and 12C are respective diagrammatic illustrations of another embodiment utilizing a single track of LEDs comprised of a series of LED modules connected together at adjustable angles to permit the track to be bent to simulate different pitch types.

DETAILED DESCRIPTION OF EMBODIMENTS

Specific dimensions set forth below or incorporated herein by reference are by way of example for particular embodiments to assist in an understanding of the illustrated structure; these dimensions are not to be construed as limiting the scope of the invention.

Figure 1:
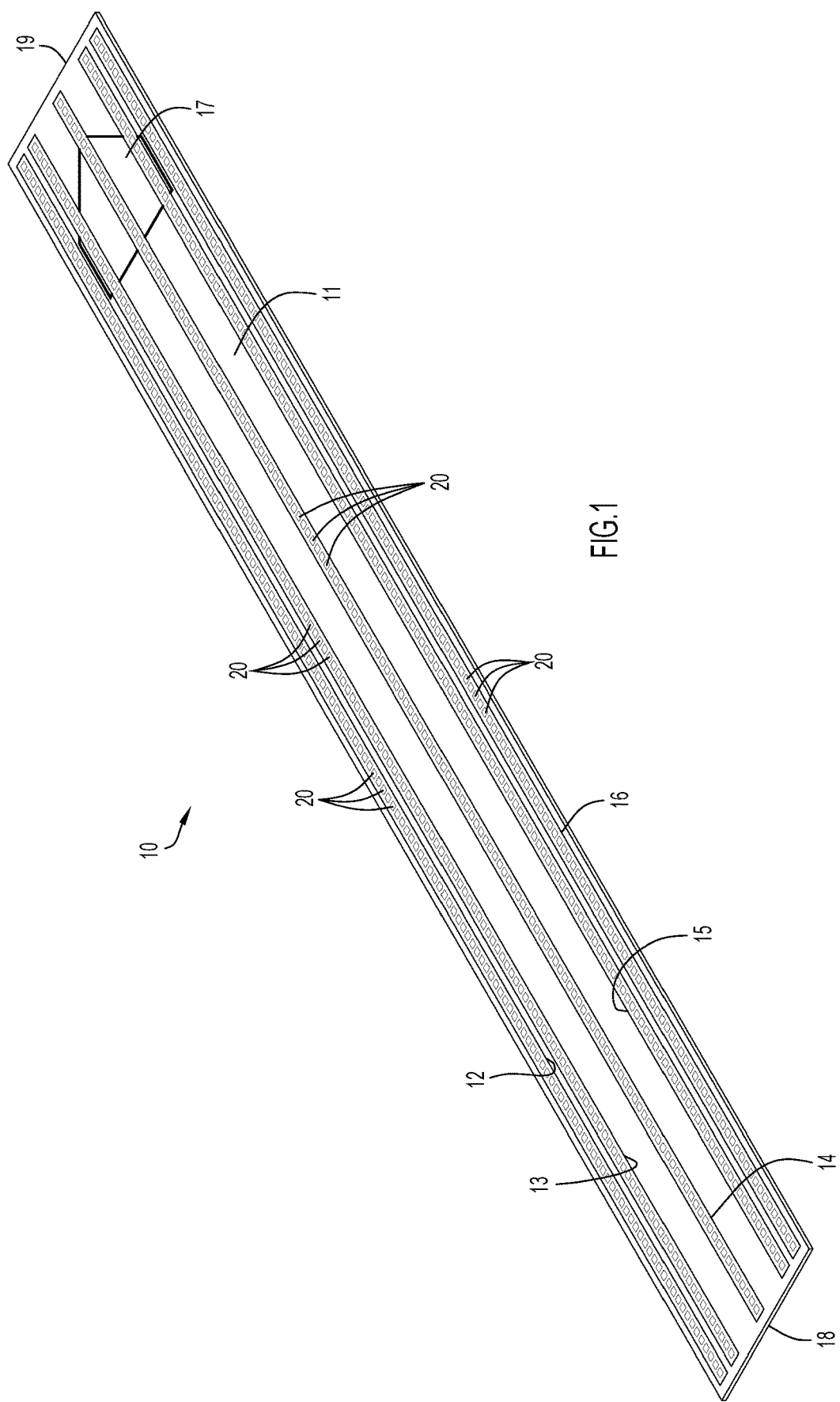
FIG. 1 is a prospective view from above of mat having five tracks of LEDs secured on its top surface and a home plate positioned as a target on the map.
Figure 2:
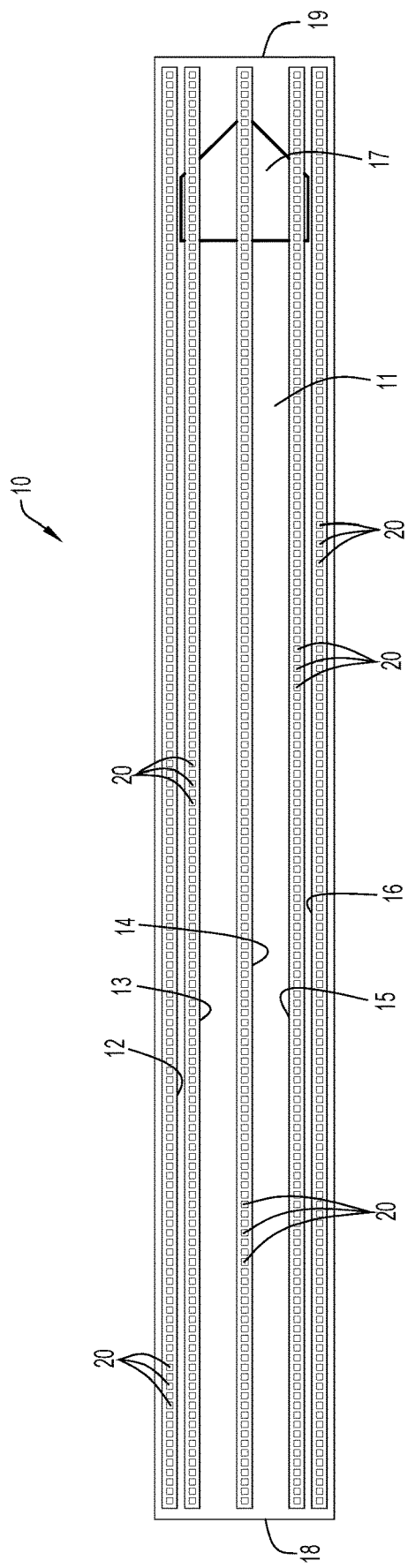
FIG. 2 is a top view in plan of the mat and target of FIG. 1.
Figure 3:
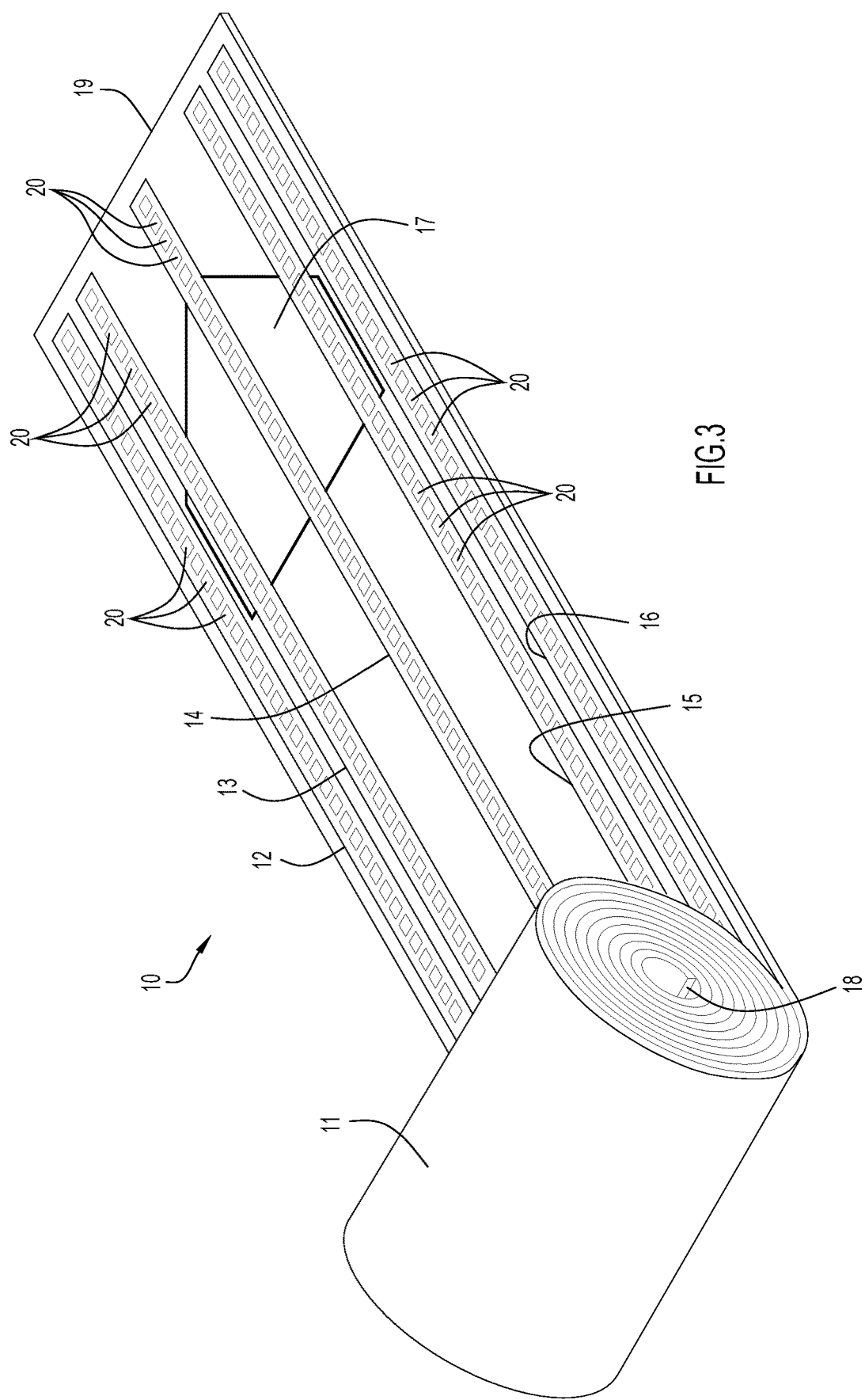
FIG. 3 is a prospective view from above showing the mat of FIG. 1 partially rolled up.

Referring specifically to FIGS. 1-3, an apparatus 10 is configured to be used in testing visual tracking and reaction time of a baseball or softball batter to a pitched ball. The apparatus comprises a substrate which in this embodiment is an elongate flexible mat 11 having a proximal or origin end 18 and a distal or target end 19. Five flexible strips or tracks 12, 13, 14, 15 and 16 are secured to the top surface of mat 11, the tracks extending in spaced parallel relation from proximate an origin end 18 of the mat to proximate an opposite target end 19. Each track has a series of longitudinally spaced light emitting diodes (LEDs) 20 secured thereon so as to be visible from above the mat, thereby defining a visible array of LEDs. The longitudinal on-center spacing between LEDs 20 in each track 12-16 is preferably uniform and is typically between 1.0 and 1.5 inches with, for example, approximately one-hundred fifty LEDs in each track. Such tracks or strips are commonly commercially available, for example the SK6812/WS2812B-Based LED Strips sold by Pololu Corporation of Las Vegas Nev., and alternatively may have any of a variety of individually addressable LED strip designs and configurations such as those illustrated and described in U.S. Pat. No. 6,016,038 (Mueller et al) and US20140290824 (Goldwater), the entire disclosures in which are incorporated herein by reference.

A target 17 in the form of a home plate is shown located proximate the target end 19 of mat 11 in a transversely centered position. It should be noted that the home plate may be separable from the mat and movable to different longitudinal or transverse positions. In the transversely centered position shown, center track 14 longitudinally bisects home plate 17, inboard tracks 13 and 15 intersect home plate on opposite sides of center track 11, and outboard tracks 12 and 16 are transversely spaced from home plate 17. In the example shown, the transverse spacing between center track 14 and each inboard track 13, 15 is the same, and the spacing between center track 14 and each of outboard tracks 12 and 16 is the same, thereby providing the tracks in a transversely symmetrical orientation with respect to home plate 17. In one embodiment example, wherein home plate is configured as a standard home plate having a width and length of seventeen inches, the spacing between center track 14 and each of inboard tracks 13 and 15 is approximately 6.8 inches, and the spacing between center track 14 and each of outboard track 12 and 16 is approximately 9.8 inches. In this embodiment the mat length may be 16.4 feet (i.e., 5 meters) long, permitting it to be used in confined spaces that cannot accommodate the 60.5 feet distance between a baseball pitcher's mound and home plate or even the approximately forty feet distance between a softball pithing rubber and home plate.

Mat 11 is made from a flexible material, typically plastic and ideally a plastic mesh to minimize weight, so that it can be rolled up about a transverse axis, shown in FIG. 3, and carried from place to place. The roll up may be with the top surface of the mat on which the LED tracks are mounted interiorly disposed as shown in FIG. 3; alternatively the mat may be rolled up with the tracks exteriorly disposed, i.e., with the LEDs facing radially outward from the roll.

Figure 8:
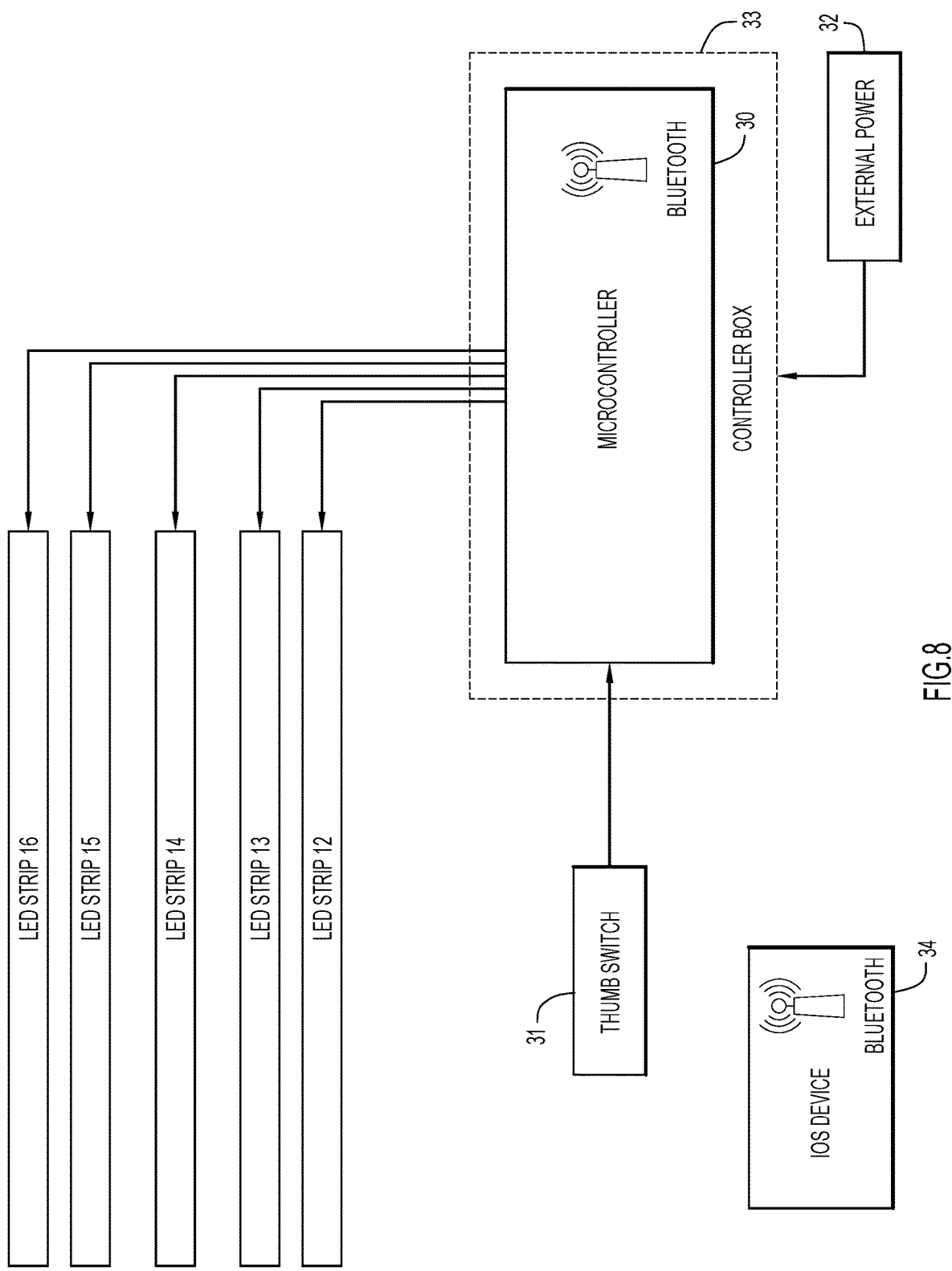
FIG. 8 is an electrical block diagram showing a controller connected to the mat of FIG. 1 along with a trainer controller and a user actuator switch.

When used to test and improve a batter's visual tracking skills and reaction time to a baseball or softball pitch, actuation of the LEDs 20 is under the control of a controller illustrated in the schematic diagram of FIG. 8. Specifically, with reference to both FIGS. 1 and 8, controller 33 is powered from an external power source 32 such as a. c. convenience power. Controller 33 includes a microcontroller 30 which may be any central processing unit (CPU), particularly a microprocessor, connected to individually illuminate the LEDs 20 in any of several stored sequences, each sequence corresponding to a simulated baseball or softball pitch path involving the LEDs on one or more tracks 12-16.

For each of the selectable pitch paths LEDs are actuated in a sequence beginning at origin end 18 and proceeding toward the target end 19. For some selectable pitch paths all of the sequentially actuated LEDs 20 reside on the same track; this corresponds to a straight pitch, typically, but not necessarily, a fastball. For other selectable pitch paths the sequentially actuated LEDs reside in two or more tracks, the sequence switching to an adjacent track at some distance along mat 11 according to the programmed sequence for the selected pitch path; this would correspond to a curve ball, slider, a tailing fastball or other breaking pitch. In addition, the selectable pitch paths stored in microcontroller 30 may simulate pitches of different speeds, an effect determined by the rate of successive actuations of the LEDs in the selected pitch. Further, selectable pitches may be programmed to be either strikes, in which case the pitch crosses home plate 17 in either of tracks 13, 14 or 15, or balls, in which cases the pitch passes home plate 17 in either of the outboard tracks 12 or 16.

A trainee or user of the system may be provided with a user actuator such as a manually actuable electrical switch 31, typically a thumb switch, that electrically communicates with the microcontroller 30. The user-trainee is typically instructed to actuate the switch when the sequence of LED actuations in the selected pitch path reaches a designated object LED proximate the home plate target 17. The microcontroller is programmed to compare the time of switch actuation with the time of actuation of that object LED, and any temporal difference serves as a measure of the user's reaction time and ability visually track a simulated pitch. The object LED is typically chosen for a particular exercise according to the pitch location for which the trainee is practicing. Thus, the object LED may reside in any of the tracks but would most commonly reside in the center track 14 or either of the inboard track 13 or 15 since those track intersect with home plate. Likewise, the object LED may be located slightly forward (i.e., toward the origin location) of home plate 17 or at home plate. The time occurrence of particular simulated pitches (i.e., straight, breaking, different speeds, etc.) may be programmed to be random or in a fixed order, or may be manually selected by a trainer controlling operation of the microcontroller 30. Such control may be effected by a trainer's selector connected by wire to the microcontroller, or by a remote controller 34, for example a smart phone, communicating wirelessly by blue tooth technology, or the like, with the microcontroller and programmed with appropriate mobile application software.

Figure 4:
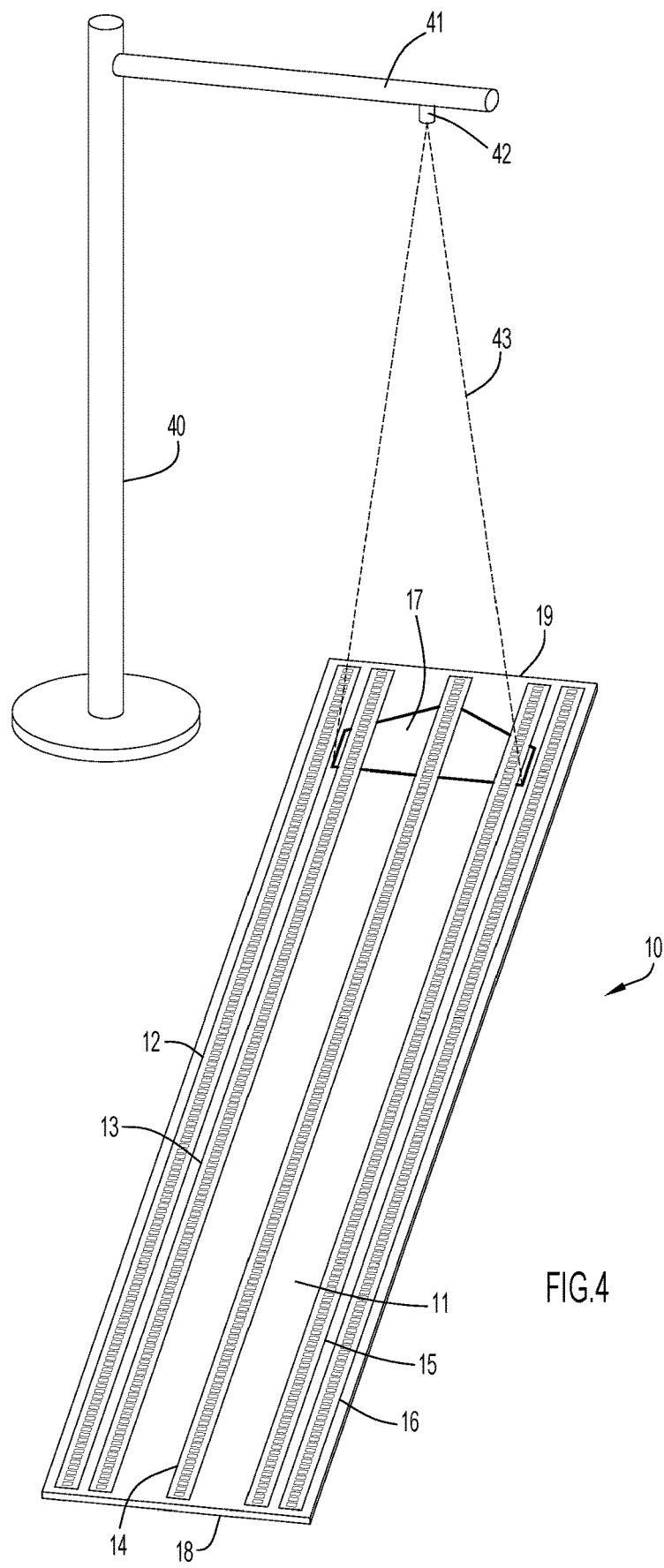
FIG. 4 is a perspective view from above showing the mat and target of FIG. 1 employed with an energy beam transmitter and receiver.

Instead of an electrical switch, the user actuator may be a baseball bat arranged to be swung over home plate to briefly interrupt a vertical energy beam as illustrated in FIG. 4. More particularly, a vertical support 40 has a horizontal extension 41 from its upper end. The extension 41 carries an energy beam transmitter 42 such as a source of infra-red (IR) energy configured transmit an IR beam 43 downward toward home plate 17. IR receivers (not shown) embedded in home plate 17 are in electrical communication with microcontroller 30 and are positioned to detect when a bat or other object is moved over the home plate and interrupts the beam. The time of interruption is detected at the microcontroller and compared to the actuation of a designated object LED 20 as described above. The number and positions of IR receivers on and around home plate in various embodiments of the system permit users and trainers to collect varying degrees of detail regarding the reaction time and visual tracking ability of a batter-trainee.

Instead of separate energy beam transmitters and receivers, another embodiment of the system illustrated in FIG. 5 employs one or more energy beam transceivers capable of both transmitting the energy beam and receiving reflections therefrom. Specifically, two transceivers 44 and 45 may be provided on home plate 17, for example proximate the leading edge of home plate 17, transversely spaced on opposite sides of center track 14. When a bat or other object is swung and breaks the combined beam 46, the reflection from the bat is sensed at the transceivers which are in electrical communication with microcontroller 30. The time between the reflection and actuation of a designated object LED is determined at the microcontroller.

Figure 6A:
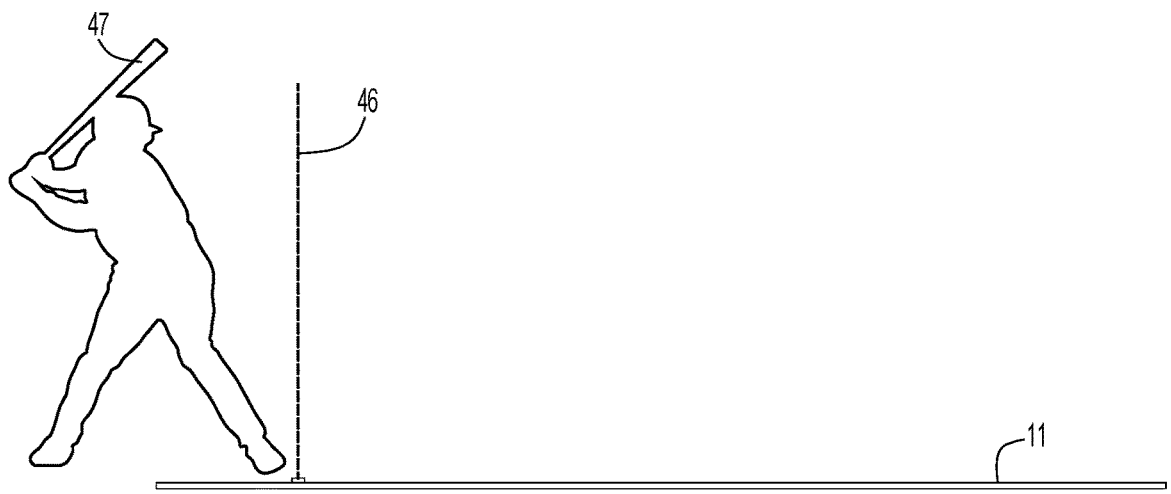
FIGS. 6A, 6B and 6C are diagrammatic views in elevation showing a user in respective stages of swinging a bat and interrupting the energy beam generated in the embodiments of FIGS. 4 and 5.
Figure 6B:
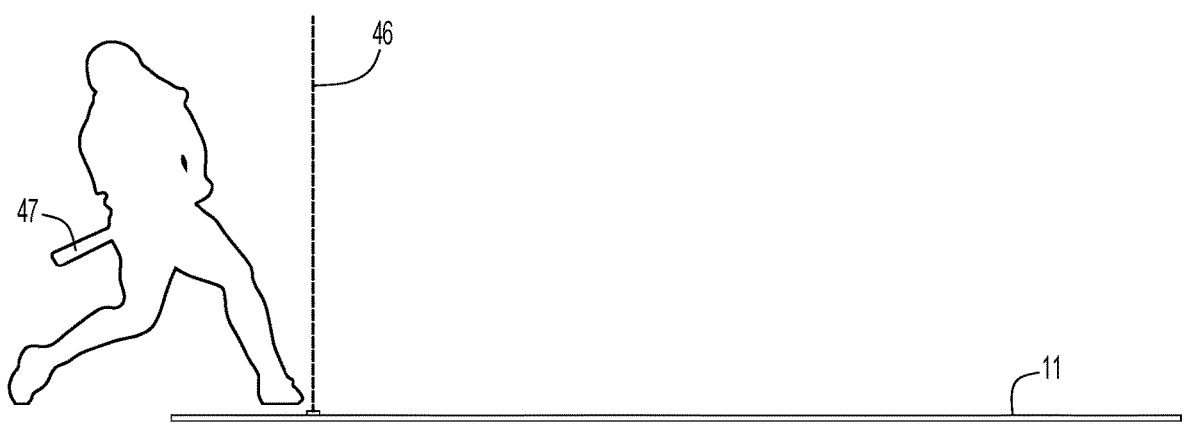
Figure 6C:
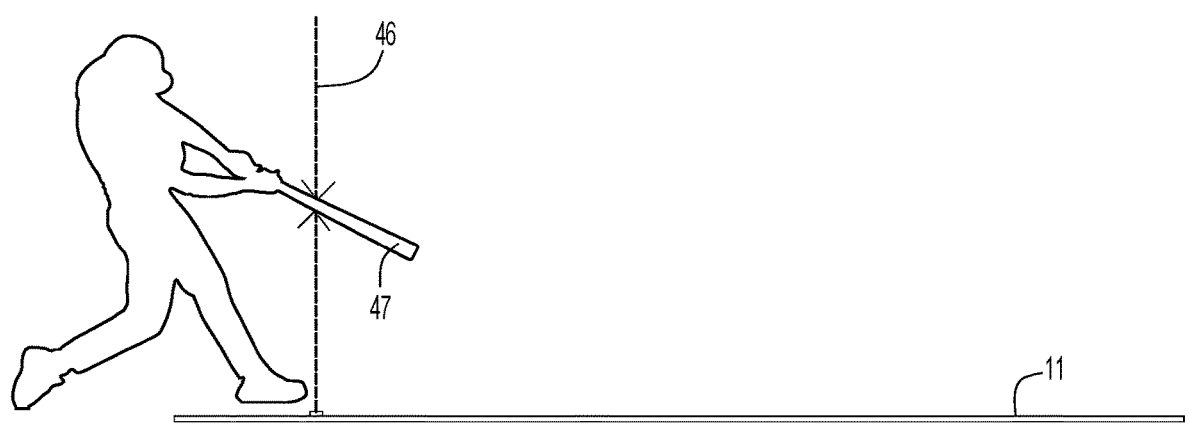

FIGS. 6A, 6B and 6C diagrammatically show successive stages of a trainee-batter tracking a simulated pitch along mat 11 and swinging a bat 47. The objective, as described above, is to break the beam 46 in time coincidence with actuation of the selected object LED during a sequence of LED actuation for a selected simulated pitch. In this arrangement the energy beam is substantially planar and positioned in vertical alignment with the designated object LED.

FIG. 7A schematically illustrates track 14 to show the track dimensions in one example embodiment. As shown, the track is five meters (16.4 feet) in length, and the on-center longitudinal spacing between successive LEDs 20 is 33 mm (1.23 inches).

In order to assist the user-batter in recognizing balls and strikes locations relative to home plate, the light sources, i.e., LEDs 20, are configured to emit different light colors, depending on the simulated pitch. For example, in one embodiment, if a right handed batter steps up to the mat and addresses home plate 17, each of the LEDs in the outboard tracks 12 and 16 when actuated might be set emit a yellow light, each of the LEDs in center track 14 when actuated might be set to emit a green light, each of the LEDs in inboard track 15 when proximate the batter when actuated might be set to emit a blue light, and each of the LEDs in the inboard track 15 away from the batter when actuated might be set to emit a red light. For a left hand batter the colors in inboard tracks 13 and 15 might be reversed. Other colors may be selected based on batting strategies and use color to assist in pitch recognition.

Figure 9:
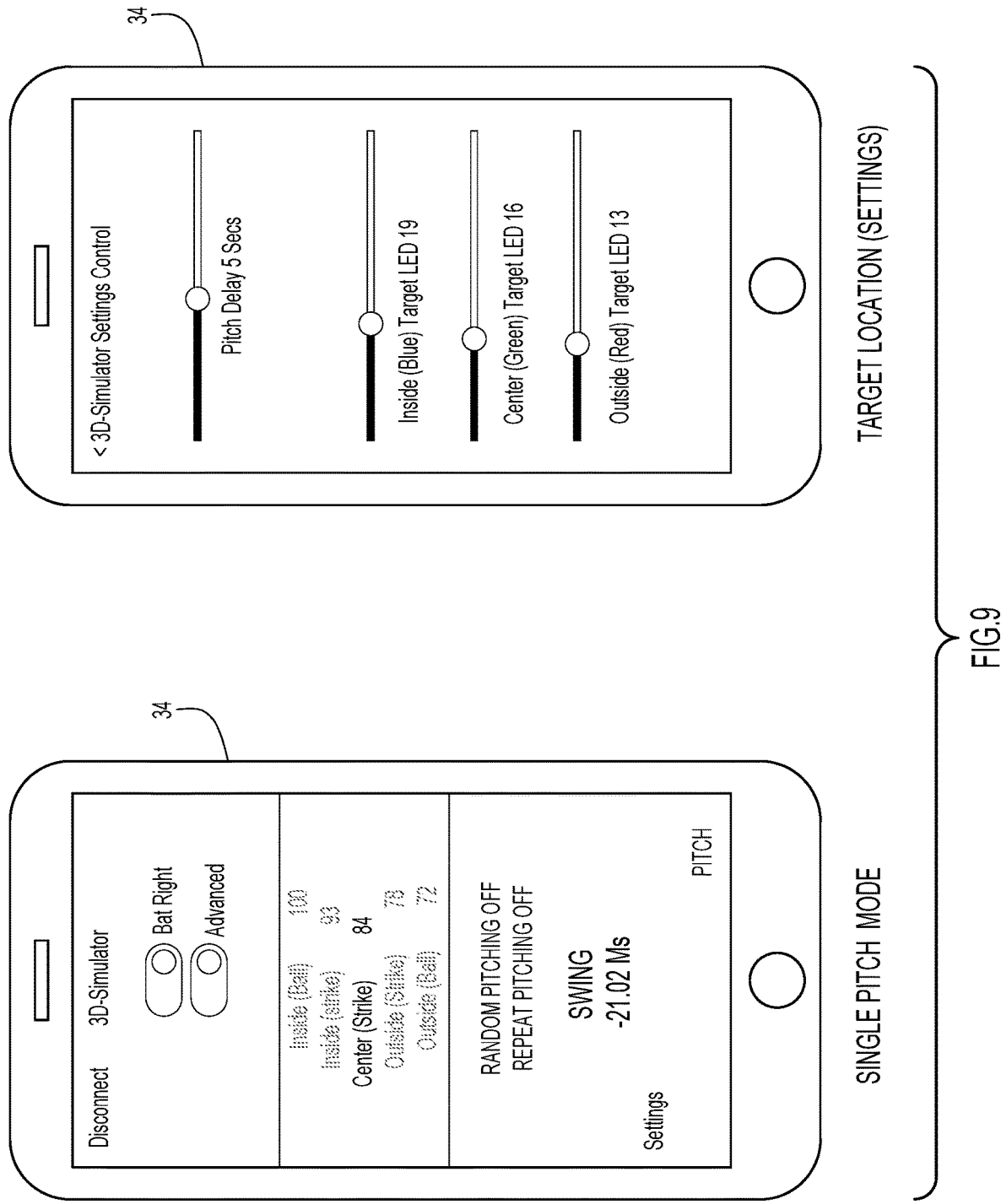
FIG. 9 is shows two screens of a smart phone employing a mobile application for controlling operation of the controller of FIG. 8.

FIG. 9 diagrammatically illustrates examples of screen shots at the trainer's remote controller 34 in both a single pitch mode and for target location settings. In particular, the trainer can set the object LED, i.e., the LED located at the intended swing point in the current LED sequence. When an LED simulated pitch sequence is initiated, the user-batter tries to stop the sequence at the object LED location, and a result is displayed on the screen at unit 34 indicating the time difference between the beam break or switch actuation (i.e., when the sequence is stopped) and the time of actuation of the object LED. The result may be a negative number indicating the batter swings early (i.e., the sequence was stopped prior to reaching the object LED location), a positive number if the batter swings late (i.e., the sequence was stopped after passing the target LED location), or zero if the swing is correctly timed (i.e., if the sequence was stopped at the object LED location). Test results may be collected for statistical analysis.

As shown in the single pitch mode in FIG. 9, the trainer may select pitches for right or left handed batters. In addition, when the advanced mode is selected, simulated pitching speeds correspond to those for baseball; when the advanced mode is not selected the simulated pitching speeds correspond to those for fast pitch softball or other applications programmed into the system.

The microcontroller 30 may use Bluetooth Low Energy (BLE) wireless personal area network technology to communicate with controller 34. In such case the microcontroller 30 acts as a peripheral node in the protocol and advertises it as a connectable node. When the app is run on the controller 34 a scan is initiated to look for devices to which to connect. Once the node is selected a connection is established and controller 34 device acts as the central node (master). Communication at a low level is a 9600 baud serial link where groups of bytes are sent between the central node and the peripheral with checksums to detect transmission errors.

The substrate on which the tracks are mounted need not be in the form of a flexible mat but instead may be a rigid structure. To preserve the desired portability, the rigid structure may be in the form of separable rectangular panels 11a, 11b, 11c, 11d and 11e as illustrated in FIGS. 10A and 10B. Each panel has a respective length of the five LED tracks secured thereto. Specifically, panel 11a has track portions 12a, 13a, 14a 15a and 16a secured to its top surface; panel 11b has track portions 12b, 13b, 14b 15b and 16b secured to its top surface; etc. When the panels are joined end to end as shown in FIG. 10A, the track sections of adjacent panels interconnect structurally and electrically so that the panels form the overall substrate structure. In FIG. 10B the panels are shown in slightly spaced sequential relation, prior to being joined.

Figure 11A:
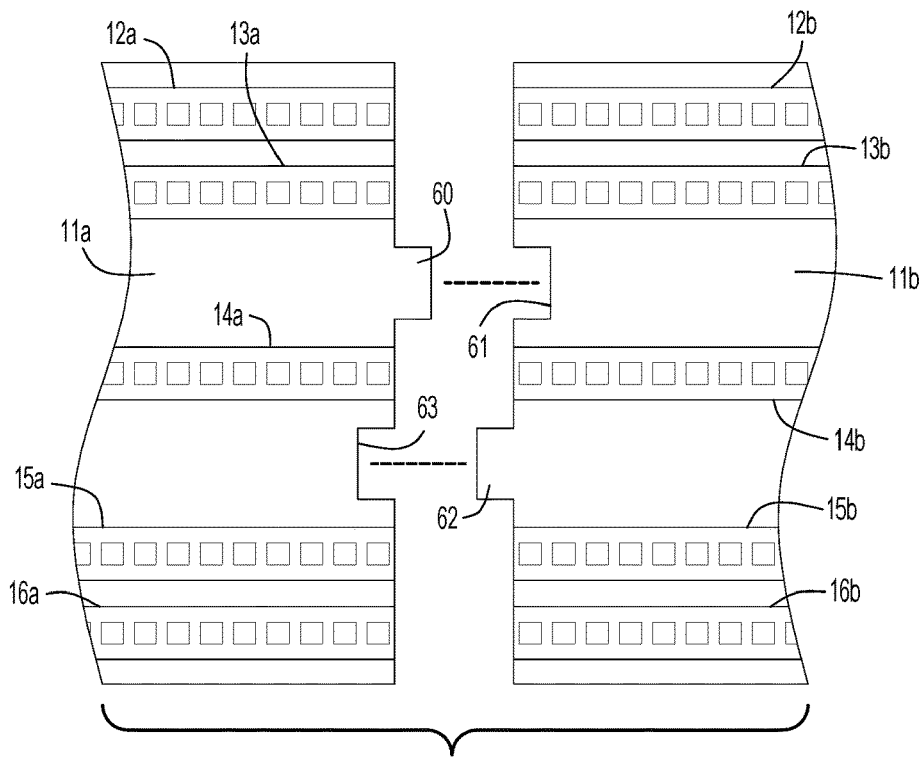
FIG. 11A is a partial view in plan showing two of the separable boards of FIGS. 10A and 10B being structurally connected.
Figure 11B:
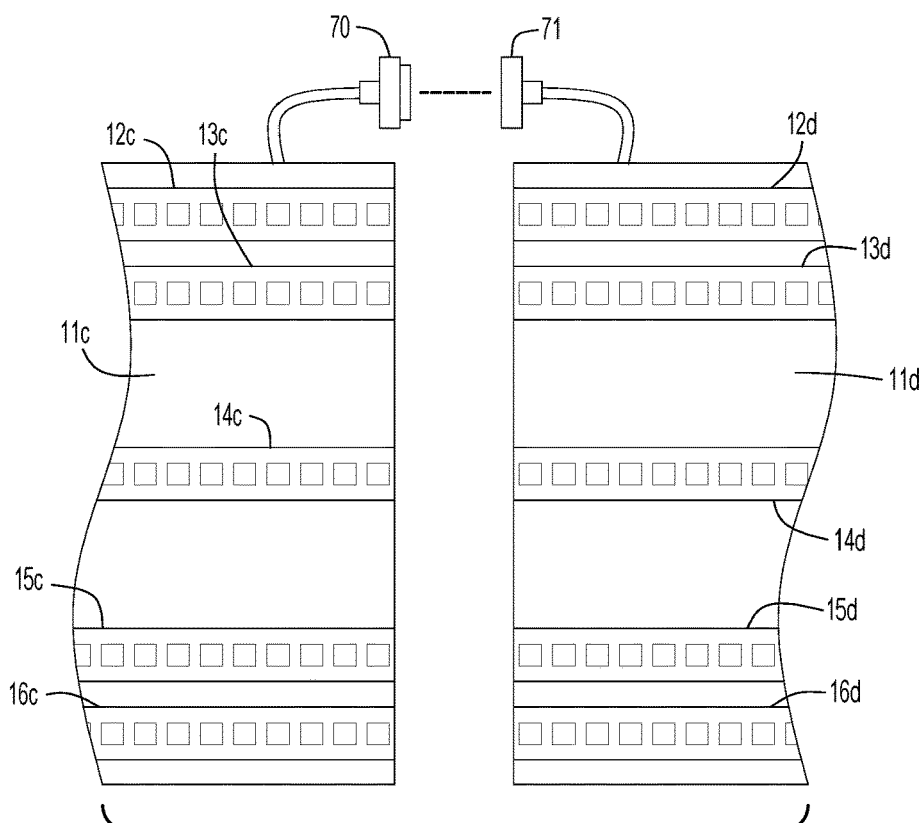
FIG. 11B is a partial view in plan showing two of the separable boards of FIGS. 10A and 10B being electrically connected.

FIG. 11A illustrates one way of structurally joining the panels. Specifically, joining of panels 11a and 11b is illustrated by way of example. Structural engagement is effected by a pair of mortise and tenon joints wherein a tenon 60 projecting longitudinally from the distally facing edge of panel 11 on one side of center track section 14a engages a mortise 61 recessed into the proximally facing edge of panel 11b on the same side of track section 14b. Likewise, a tenon 62 projecting longitudinally from the proximally facing edge of panel 11b on the opposite side of track section 14b engages a mortise 63 recessed into the proximally facing edge of panel 11b on the same side of track section 14a. The tenon and mortise connection may be a friction fit, a dovetail fit or any other fit that maintains the panels in place while in use. The ends of the track sections in the thusly joined panels may abut to assure electrical connection continuity, or the electrical connections may be provided by separate electrical connectors 70, 71 as shown in FIG. 11. Alternatively, the joints between the panels may be hinged so that the panels can be folded onto one another without becoming totally disengaged.

In a simplified alternative embodiment, illustrated in FIGS. 12A 12B and 12C, a single LED strip may serve is provided as a single track that may have selected bends at different points along its length to provide straight or selectively curved paths. Specifically, the track includes multiple LED modules 51 of plural longitudinally spaced LEDs connected in a series end to end by connectors 50 that permit adjacent fixtures to extend from one another at adjustable angles in a common plane. Modules and connector structures of this type are known, as exemplified in US20140362572 (Barrett) and US20140307438 (Pearson et al), the entire disclosures of which are incorporated herein by reference. The track may be bent to simulate breaking pitches as shown in FIGS. 12A and 12C, or it may be configured in a straight line to simulate a straight pitch as shown in FIG. 12B. In this simplified system the microcontroller does not select the type of pitch (i.e., straight, curved, etc.) but can control the speed and times of the pitches.

Figure 13C:
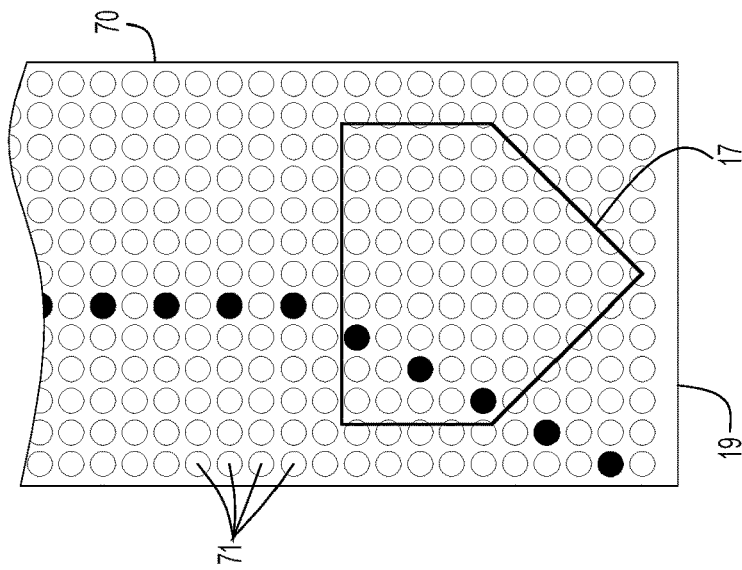
FIGS. 13a, 13B and 13C are respective diagrammatic illustrations of yet another embodiment in which selectively and individually actuable LEDs are provided in a matrix to simulate different pitch types.
Figure 13B:
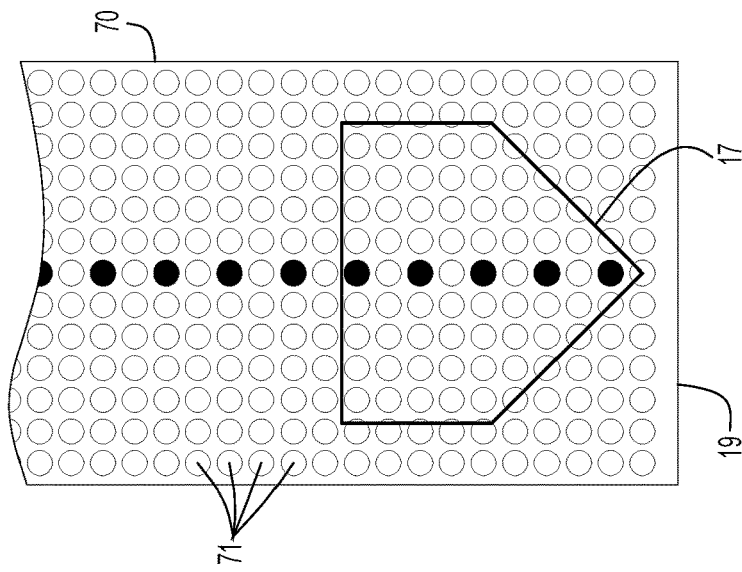
Figure 13A:
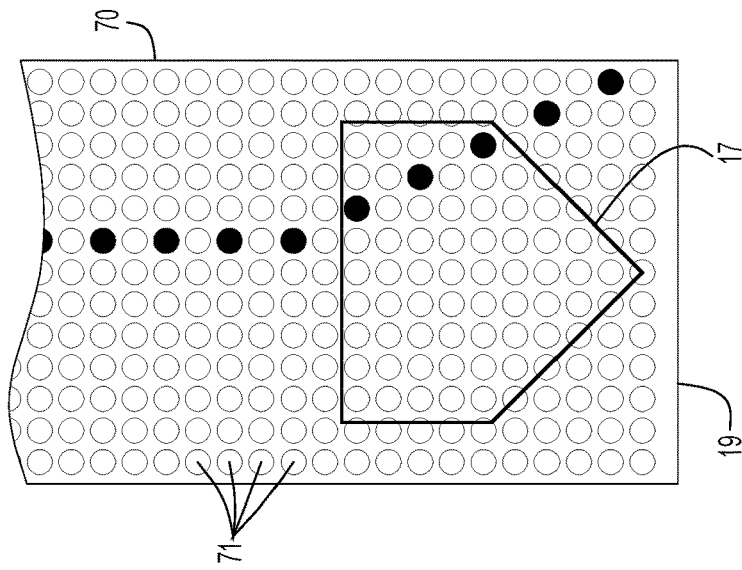

In still another embodiment, illustrated in FIGS. 13A, 13B and 13C, the substrate 60 has on its top surface a rectangular matrix array of individually addressable LEDs 61 arranged in multiple columns extending longitudinally and rows extending transversely. The multiple columns may be viewed as respective multiple tracks. Selectable pitch paths are executed by the microcontroller by sequentially actuating the appropriate LEDs for the selected path. Thus for a pitch breaking away from a right hand batter, the LEDs shown in black in FIG. 13A are sequentially illuminated, the sequence being at a desired illumination rate to simulate the pitch speed. Likewise, for a pitch breaking away from a left hand batter, the LEDs shown in black in FIG. 13C are sequentially illuminated at a desired illumination rate to simulate the pitch speed. For a straight pitch as shown in FIG. 13B the LEDs shown in black are sequentially illuminated at a desired illumination rate to simulate the pitch speed.

It will be appreciated that one of the purposes of the invention is for the training device to serve as a portable simulated batting cage that can be used indoors. It is intended to be simple, rugged, and lightweight. In one operation mode example, the trainer/instructor or user simply rolls out the mat, or assembles the panels, and makes the connections to the controller box. For sequential pitches the time intervals between successive pitches may be selectively set. Pitch sequences can be actuated in manual (one-shot) modes as well as sequential pitch modes where the same pitch may be repeated or different pitches are sequentially sent, randomly or by program. There is a setting to select right or left handed batter so the color mapping of the mat is identical for both stances. When a pitch is actuated from the IOS device the microprocessor responds and begins the test. The LEDs at the origin location end of the substrate cycle red, yellow, and green, each with an on time of one second, indicating the sequence is about to begin; then the simulated pitch is initiated. As LED are sequentially actuated longitudinally along the substrate, the trainee/player will attempt to stop the sequence by actuating the user actuator (e.g., the momentary thumb switch, a bat, etc.). The microprocessor samples the status of the switch/bat during the pitch sequence until the switch is actuated or the bat breaks the energy beam. That time is compared by the microprocessor to the time at which the pitch sequence reaches the object LED which is typically selected by the trainer. The time difference is a measure of the trainee's visual tracking and reaction time. Each pitch has one of the following indicated results: for balls, swing or no swing; for strikes, swing or no swing and the swing latency in milliseconds relative to the target LED location.

As disclosed one device for use as a user actuator is a simple infrared (IR) beam-breaker. The beam-breaker uses a beam emitter suspended on an inverted tee with the receiver attached to the home plate to detect the trainee swinging a bat through the beam.

Although the invention is described herein for simulating pitches in training a baseball batter, it will be understood that other uses are possible. For example, the invention may be used to train tennis players in timing their strokes. Or, if one or more LED strips are supported vertically, a basketball player's jump timing for rebounding purposes may be monitored.

Having described preferred embodiments of new and improved methods and apparatus for testing and improving a user's visual tracking skills and reaction time to a moving object, it is believed that other modifications, variations and changes will be suggested to those skilled in the art in view of the teachings set forth herein. It is therefore to be understood that all such variations, modifications and changes are believed to fall within the scope of the present invention as defined by the appended claims. Although specific terms are employed herein, they are used in a generic and descriptive sense only and not for purposes of limitation.

What is claimed is:

1. A system for testing and improving a user's visual tracking skills and reaction time to a moving object, said system comprising:
   an elongated structure having a top surface, an origin location and a target longitudinally spaced from said origin location along said top surface, said target having a width disposed transverse to the longitudinal spacing between the origin location and said target; and
   a plurality of longitudinally extending tracks secured to said structure and extending longitudinally between said origin location and said target, each track comprising a series of longitudinally spaced individually actuable light sources, wherein said tracks are transversely spaced at said target by less than the width of said target such that at least a first of said tracks intersects said target and at least a second of said tracks does not intersect said target.

2. The system of claim 1 further comprising:
   a controller including a processor connected to control sequential momentary actuation of said light sources in accordance with multiple individually selectable paths, each path comprising a respective longitudinal actuation sequence of light sources along one or more of said tracks to simulate longitudinal motion of the moving object, at least some of said paths including light sources in only one of said tracks and others of said paths including light sources in at least two of said tracks.

3. The system of claim 2 further comprising:
   a user actuator in electrical communication with said controller to enable termination by the user at any time of a then active actuation sequence of light sources.

4. The system of claim 3 wherein one of said light sources is designated as an object light source based on its proximity to said target, wherein the user is tasked with actuating the user actuator in time coincidence with actuation of the object light source, and wherein the processor is configured to measure the user's reaction time by measuring the time between actuation of the object light source and termination of an actuation sequence by the user actuator.

5. The system of claim 3 configured for testing and visually tracking the moving object as a simulated baseball pitch, wherein the target is a standard home plate, wherein said at least some of said paths simulate a straight pitch and said others of said paths simulate a curved pitch.

6. The system of claim 5 wherein said plurality of tracks comprises five parallel tracks including;
   a first center track longitudinally bisecting the home plate;
   second and third inboard tracks disposed transversely equally spaced from and on opposite sides of said first track and intersecting the home plate; and
   fourth and fifth outboard tracks disposed transversely equally spaced from and on opposite sides of said first track and transversely spaced from the home plate.

7. The system of claim 6 wherein the light sources are LEDs and wherein the LEDs in the center track emit light of a first color, wherein the LEDs in the second and third tracks emit light of second and third colors respectively different from said first color, and wherein the LEDs in the fourth and fifth tracks emit light of a fourth color different for the first, second and third colors.

8. The system of claim 6 wherein said second and third tracks are spaced from said first track by approximately 6.8 inches, and said fourth and fifth tracks are spaced from said first track by approximately 9.8 inches.

9. The system of claim 5 further characterized in that said tracks have a predetermined path length, and wherein said processor includes means for correlating said longitudinal actuation sequence of light sources along one or more of said tracks to simulated speeds of baseball pitches taking into consideration the length of said tracks compared to the distance between an actual pitcher's mound and an actual home plate.

10. The system of claim 4 wherein said user actuator is a hand-held electrical switch.

11. The system of claim 4 wherein said actuator is a user-movable member, said system further comprising:
    an energy source positioned to vertically radiate an energy beam proximate said target; and
    an energy beam detector positioned to receive said energy beam and in electrical communication with said controller;
    wherein actuation of the user actuator is interruption of the energy beam between the energy source and beam detector by said user-movable member.

12. The system of claim 1 wherein said structure is a mat capable of being rolled up about an axis transverse to its length.

13. The system of claim 1 wherein said structure is a plurality of rigid panels arranged longitudinally end to end and movable relative to one another.

14. The system of claim 1 wherein the light sources are LEDs and wherein the LEDs in the first of said tracks emit light of a first color and the LEDs in the second of the tracks emit light of a second color different from the first color.

* * * * *